(12) United States Patent
Samuelsson et al.

(10) Patent No.: US 9,044,201 B2
(45) Date of Patent: Jun. 2, 2015

(54) WIRELESS COMMUNICATION OF PHYSIOLOGICAL VARIABLES USING SPREAD SPECTRUM

(75) Inventors: Magnus Samuelsson, Danderyd (SE); Sauli Tulkki, Phuket (TH)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 2621 days.

(21) Appl. No.: 11/312,640

(22) Filed: Dec. 21, 2005

(65) Prior Publication Data
US 2006/0161224 A1    Jul. 20, 2006

Related U.S. Application Data

(63) Continuation-in-part of application No. 10/888,510, filed on Jul. 12, 2004.

(51) Int. Cl.
| | |
|---|---|
| *A61B 5/00* | (2006.01) |
| *A61M 25/00* | (2006.01) |
| *A61B 5/02* | (2006.01) |
| A61B 5/01 | (2006.01) |
| A61B 5/0215 | (2006.01) |

(52) U.S. Cl.
CPC .............. *A61B 5/6851* (2013.01); *A61B 5/01* (2013.01); *A61B 5/02007* (2013.01); *A61B 5/0215* (2013.01); *A61B 5/002* (2013.01)

(58) Field of Classification Search
USPC ............ 600/585, 462, 561; 607/60, 309, 310; 725/10
See application file for complete search history.

(56) References Cited

U.S. PATENT DOCUMENTS

| 4,026,276 A | | 5/1977 | Chubbuck | |
|---|---|---|---|---|
| 5,687,717 A | * | 11/1997 | Halpern et al. | ............... 600/300 |
| 5,704,352 A | | 1/1998 | Tremblay et al. | |
| 5,767,791 A | * | 6/1998 | Stoop et al. | .............. 340/870.11 |

(Continued)

FOREIGN PATENT DOCUMENTS

| EP | 1 136 033 A1 | 9/2001 |
|---|---|---|
| EP | 1 260 175 A2 | 11/2002 |

(Continued)

OTHER PUBLICATIONS

Robert Puers, "Linking Sensors with Telemetry: Impact on the System Design," 8th International Conference on Solid-State Sensors and Actuators, Eurosensors IX, Jun. 25-29, 1995, pp. 47-50.

*Primary Examiner* — Brian Szmal
(74) *Attorney, Agent, or Firm* — Foley & Lardner LLP

(57) ABSTRACT

The present invention relates to a system and a method of measuring a physiological variable in a body. A basic idea of the present invention is to measure a physiological variable in a body by means of employing a sensor (314) which is arranged to be disposed in the body for measuring the physiological variable. The sensor must be provided with a supply voltage in order to be operable. Therefore, a control unit (322) disposed outside the body provides this supply voltage to the sensor. The control unit also receives, from the sensor, via a wired connection (311), signals that represent the physiological variables that are measured. The control unit is arranged with a communication interface (401, 701) and a modulator (301) for wireless spread spectrum communication of the measured physiological variables for presentation purposes.

38 Claims, 10 Drawing Sheets

(56) References Cited

U.S. PATENT DOCUMENTS

| | | | |
|---|---|---|---|
| 6,016,449 A * | 1/2000 | Fischell et al. | 607/45 |
| 6,167,763 B1 | 1/2001 | Tenerz et al. | |
| 6,248,080 B1 | 6/2001 | Miesel et al. | |
| 6,336,906 B1 | 1/2002 | Hammarstroem et al. | |
| 6,428,336 B1 * | 8/2002 | Akerfeldt | 439/263 |
| 6,473,652 B1 * | 10/2002 | Sarwal et al. | 607/62 |
| 6,533,733 B1 * | 3/2003 | Ericson et al. | 600/561 |
| 6,615,067 B2 | 9/2003 | Hoek et al. | |
| 6,692,446 B2 | 2/2004 | Hoek | |
| 6,721,772 B1 * | 4/2004 | Green et al. | 708/497 |
| 6,792,311 B2 * | 9/2004 | Fox et al. | 607/31 |
| 6,960,968 B2 * | 11/2005 | Odendaal et al. | 333/219 |
| 7,065,409 B2 * | 6/2006 | Mazar | 607/60 |
| 2001/0045899 A1 * | 11/2001 | Hoek | 340/870.28 |
| 2002/0049371 A1 | 4/2002 | Lai et al. | |
| 2003/0028128 A1 * | 2/2003 | Tenerz | 600/585 |
| 2003/0126593 A1 * | 7/2003 | Mault | 725/10 |

FOREIGN PATENT DOCUMENTS

| | | |
|---|---|---|
| JP | 59-14843 A | 1/1984 |
| JP | 2001-299704 A | 10/2001 |
| JP | 2004-184351 A | 7/2004 |
| WO | WO 02/095675 A1 | 11/2002 |

* cited by examiner

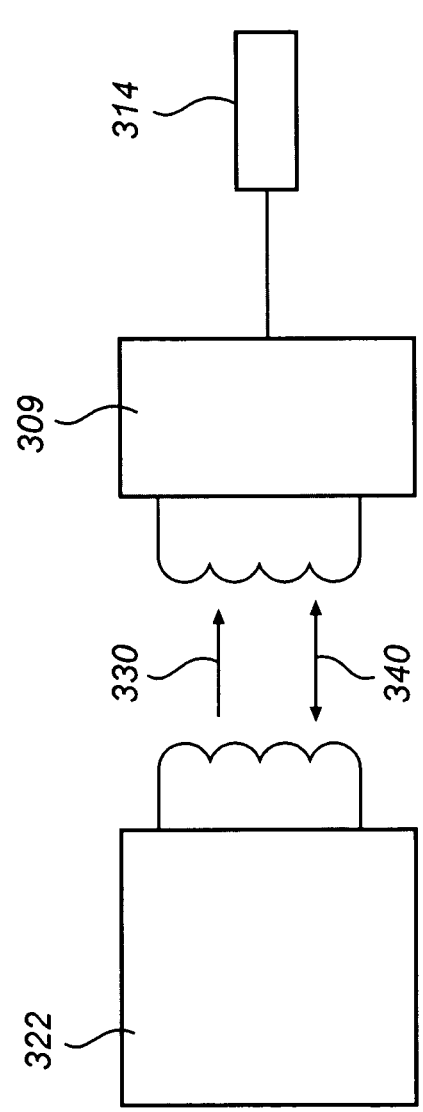

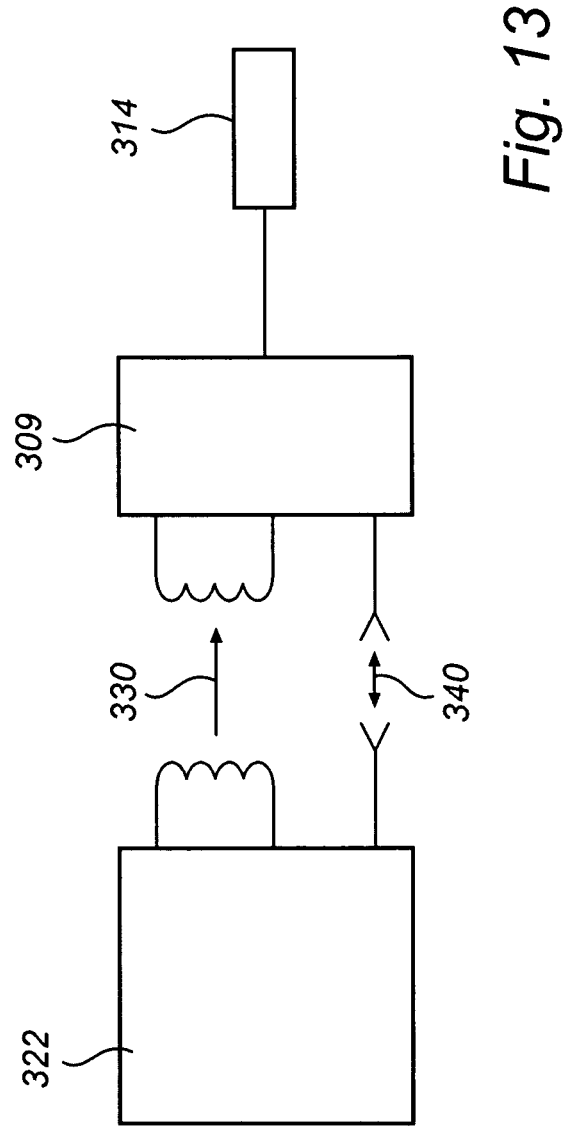

WIRELESS COMMUNICATION OF PHYSIOLOGICAL VARIABLES USING SPREAD SPECTRUM

The present application is a continuation-in-part of U.S. application Ser. No. 10/888,510, filed Jul. 12, 2004, the entire contents of which is incorporated herein by reference.

TECHNICAL FIELD OF THE INVENTION

The present invention relates to a system and a method of measuring a physiological variable in a body.

BACKGROUND ART

There is a general need for invasive measurements of physiological variables. For example, when investigating cardiovascular diseases, it is strongly desired to obtain local measurements of pressure and flow in order to evaluate the condition of the subject under measurement. Therefore, methods and devices have been developed for disposing a miniature sensor at a location where the measurements should be performed, and for communicating with the miniature sensor.

An example of a known intracranial pressure monitor is known through U.S. Pat. No. 4,026,276, in which it is described an apparatus including a passive resonant circuit having a natural frequency influenced by ambient pressure. The local pressure is measured by observation of the frequency at which energy is absorbed from an imposed electromagnetic field located externally of the cranium.

In order to communicate a measured representation of the physiological variable, devices based on acoustical as well as electromechanical interaction have been developed. In both cases, the sensor comprises a resonance element, its resonance frequency being a function of the physiological variable to be determined. Energy is radiated towards the resonance element from an external transmitter of acoustical or electromagnetic waves, respectively. The frequency of the transmitted energy is swept over a pre-selected range, and is registered by a monitoring unit. During the frequency sweep the registering unit will detect the resonance frequency of the resonance element, since a drop of the monitored transmitted energy will occur at this frequency.

The example above of a device for invasive measurements of physiological variables is an example of a passive system, i.e. the sensor inside the body does not require a source of energy, such as a battery or electricity provided via electrical leads. For guiding a sensor to a specific point of measurement during investigating cardiovascular diseases it is known to mount a miniature sensor at the distal end of a guide wire or a catheter. The guide wire or the catheter is inserted into a blood vessel such as the femoral artery, and is guided by fluoroscopy to local sites within the cardiovascular system where improper functioning is suspected.

The development of miniature sensors, or micro-sensors, for a number of physiological variables, including pressure, flow, temperature etc., constitutes a historical medical technology landmark. However, the assembly of the sensor and the associated cables and connectors is difficult to perform in a cost-efficient manner due to the small physical dimensions, the required mechanical precision and uncompromisable demands on patient safety. More specifically, it is estimated that about one third of the cost, or more, of the total manufacturing cost for such devices are traceable to connectors and cables. As a consequence, devices performing these functions are still expensive, and the spread of their use is limited to areas of highest clinical priority. The cost aspect is further emphasized by the fact that devices for invasive procedures must be regarded as disposable items, due to the risk of transmitting infectious diseases. If the cost of cables and connectors could be minimized or even eliminated, large savings would be possible.

Another problem with passive sensors of the type disclosed in U.S. Pat. No. 4,026,276 is undesired electromagnetic coupling between the transmitter/receiver on the one hand, and the sensor on the other. This coupling is due to the fact that the power supply and the signal transmission are not functionally separated. A manifestation of this problem is that the output signal of the system is influenced by the position of the sensor, which obviously is an undesired property. This problem could be overcome by adding active electronic circuitry to the sensor, including a local transmitter operating at a frequency other than the frequency used for providing electric power to the sensor and the circuitry. Thereby, the function of wireless power supply should be separated from that of signal transmission and, consequently, the output signal should not be influenced by the position of the sensor. Such a solution has been described by R. Puers, "Linking sensors with telemetry: Impact on the system design", Proc. 8.sup.th Int. Conf. Solid State Sensors and Actuators, Transducers-95, Stockholm Sweden, Jun. 25-29, 1995, Vol. 1, pp 47-50. However, a drawback of this solution is that it is difficult to miniaturize to the size desired for medical use with a guide wire. Furthermore, wideband systems of this kind are amenable to electromagnetic interference and disturbances.

Thus, there is a need for an improved communication system for communication with a sensor positioned inside a body of a subject for invasive measurement of a physiological variable, said communication system exhibiting reduced sensitivity to the position of the sensor as well as to electromagnetic interference.

U.S. Pat. No. 6,692,446 discloses a method and a device for measuring a physiological variable in a living body, whereby a transmitter is disposed outside of the body to transmit radio frequent energy, and a receiver is disposed outside of the body to receive radio frequent energy. A transponder unit having a sensor sensitive to the physical variable, and a modulator unit for controlling the radio frequent energy absorption of the transponder unit according to a time-sequence representing said physical variable, is introduced into the body. The transmitter sends radio frequent energy to the transponder, and the receiver monitors the radio energy absorption of the transponder unit to determine the time-sequence representing said physical variable. The time-sequence is decoded to interpret it as a measure of the physical variable. Thus, a wireless power supply is provided, and sensitivity to electromagnetic interference is reduced.

However, problems still remain in that the modulator unit and related circuitry is located in a direct proximity to the sensor in the transponder unit disposed in the body. Due to the fact that size requirements on the transponder unit are severe, electronic devices included in the transponder unit must be closely arranged. Moreover, due to these size requirements, it is not possible to use standard electronics in the transponder unit. This has the undesired effect that production of transponder unit electronics becomes rather complex and hence quite expensive.

SUMMARY OF THE INVENTION

An object of the present invention is to solve the above given problems and provide a system for wireless spread spectrum communication of a signal that represents a measured physiological variable by means of employing a system in which a minimum of electronics, preferably only a measuring sensor, is located inside the body, and the remaining system electronics is located outside the body.

This object is achieved by a system and a method for measuring a physiological variable in a body in accordance with the embodiments described herein.

According to a first aspect of the present invention, the system comprises a sensor arranged to be disposed in the body for measuring the physiological variable and to provide a signal representing the measured physiological variable, a control unit arranged to be disposed outside the body and a wired connection between the sensor and the control unit to provide a supply voltage from the control unit to the sensor, and to communicate the signal from the sensor to the control unit. The control unit further has a modulator for modulating a carrier signal with the received signal representing the measured physiological variable and a communication interface for wireless spread spectrum communication of the modulated signal.

According to a second aspect of the present invention, the method comprises the steps of measuring the physiological variable by means of a sensor arranged to be disposed in the body, communicating a signal representing the measured physiological variable from the sensor to a position outside the body via a wired connection, supplying the sensor with a supply voltage via the wired connection, modulating a carrier signal at the position outside the body with the signal that represents the measured physiological variable and communicating the modulated signal wirelessly to a remote position using spread spectrum.

A basic idea of the present invention is to measure a physiological variable in a body by means of employing a sensor which is arranged to be disposed in the body for measuring the physiological variable. The sensor is preferably arranged at the distal end of a guide wire for positioning the sensor within the body. Size requirements on the sensor are for obvious reasons very strict, since the sensor is inserted by means of the guide wire in a blood vessel of a living human or animal body. The sensor includes elements that are sensitive to the variable to be measured, for example temperature, flow or pressure, etc. The sensor itself is known in the art. The sensor must be provided with a supply voltage in order to be operable. Therefore, a control unit disposed outside the body provides this supply voltage to the sensor. The control unit also receives, from the sensor, signals that represent the physiological variables that are measured. Communication between the sensor and the control unit is effected by means of a wired connection, for example the guide wire on which the sensor is arranged.

The control unit is arranged with a communication interface for wireless spread spectrum communication of the measured physiological variables for presentation purposes. Communication via the wireless communication interface may be effected by means of, for example, radio frequency (RF) signals or infrared (IR) signals, or some other known technology for wireless communication. In the following, it is assumed that RF signals are employed. Hence, the control unit may, via the wireless interface, pass measured physiological variables to a display device, a computer, a monitor or some other appropriate device for presenting, registering, processing, etc. the measured variables. The control unit is further arranged with a modulator for modulating a carrier signal with the received signal that represents a measured physiological value for wireless spread spectrum communication across the radio frequency interface.

The present invention is advantageous for a number of reasons. For example, the modulator for modulating the carrier signal with the signal representing the measured physiological variable may be located at the control unit, instead of being located in the body in direct proximity to the sensor, as in prior art systems. Hence, when placing the modulator outside the body, standard modulation circuitry may be employed, as size requirements are greatly mitigated as compared to placing the modulator in the body. Also, standard circuitry are usually off-the-shelf products that are comparatively inexpensive, and time of delivery of this type of circuitry is generally short. The overall complexity of the measuring system according to the present invention, in particular when considering production, assembly and installation aspects, decreases considerably. Moreover, efficiency with regard to supply voltage provision increases as the supply voltage is provided to the sensor via the guide wire. In the prior art, when supply voltage must be transmitted through tissue of a body, the efficiency generally becomes lower. Further, communication via a wireless communication interface enables complete electrical isolation between the control unit and e.g. a monitor with which it communicates.

A spread spectrum technique is employed for communication via the wireless interface of the control unit. For spread spectrum communication, the global 2.4 GHz Industry Scientific and Medical (ISM) unlicensed band may be employed, even though any other suitable frequency band could be used. By inserting an uncorrelated pseudo-noise (PN) sequence into the "baseband" information signal, i.e. the signal representing measured physiological variables, energy used in transmitting the signal is spread over a wider bandwidth, and appears as noise. This is referred to as spreading operation. At reception of the spread signal representing the measured physiological variable, despreading is performed, wherein the PN-sequence inserted in the baseband signal is removed and the information signal is reconstituted. As a consequence, noise and interference signals are rejected since they do not contain the particular PN-sequence. A great advantage related to the usage of a spread spectrum technique for the wireless communication across the control unit interface is that the communication becomes resistant to interference and noise. Hence, communication reliability is greatly enhanced.

According to an embodiment of the present invention, the system further comprises a monitoring device arranged to demodulate the modulated signal, which modulated signal is received via the radio frequency interface, and hence provide a representation of the measured physiological variable. The monitoring device may further be arranged to supply the control unit with a supply voltage and control data via the radio frequency interface.

When performing this type of physiological measurement, there is generally a need for a monitoring device, such as a computer and an associated computer screen, for monitoring the measured variables after demodulation. Typically, the monitoring device is provided with software that allows different arithmetic operations and signal processing algorithms to be performed on the measured variables, as well as providing an environment in which the variables may be displayed in a meaningful manner, which environment may comprise diagrams, coordinate system axes, tables, curves, etc. This device is normally located on some distance from the control unit, the sensor and the object itself, e.g. a human body. Moreover, the monitoring device is typically connected to the mains supply, from which a 230V AC voltage may be provided. Since the parts of the system of the present invention that are located in vicinity of the object on which measurements are performed, i.e. the control unit, the sensor and related circuitry, preferably should be as small as possible in order to simplify management of the measurement system during operation, it is advantageous if the monitoring device can provide the system with a sufficient supply voltage, since any power source arranged at the control unit thus may be eliminated.

From the monitoring device, it may also possible to send control data to the measuring system. For example, an operator of the monitoring device may want to control the number of acquired signals from the sensor, the rate with which data is transferred, control signals to a possible microcontroller arranged at the control unit, etc. The control data should be used at the monitoring device in a modulation process of a monitor device carrier signal, in a manner such that the control data does not cause interference with the supply voltage signals that are sent from the monitoring device to the control unit via the wireless interface. Due to the fact that the interface between the monitoring device and the control unit is wireless, any cables and connectors to connect the control unit to the monitoring device will be eliminated, which is highly advantageous during operation of the system. Hence, the monitoring device should be provided with modulation circuitry in order to perform modulating operations on signals transferred across the radio frequency interface. In practice, the system may be used in an environment such as a hospital for measuring a physiological variable inside the body of a patient. Since personnel performing the measurements, by means of the system in accordance with the present invention, requires free space for movement in the vicinity of the patient, elimination of cables is highly advantageous.

In prior art, where a guide wire is connected to a monitoring device by means of an interfacing cable, there is a potential risk of leakage currents flowing from the monitoring device via the interface cable to the guide wire.

Possibly, leakage currents will flow into the body of the patient, which leakage currents are unpleasant and potentially hazardous. By means of the wireless communication interface of embodiments of the present invention, these leakage currents are eliminated.

It is possible that the monitoring device is arranged to receive a number of modulated signals from a number of control units and to provide a representation of the measured physiological variables that correspond to the received modulated signals. In that case, each control unit is arranged such that the signals sent from a specific control unit is provided with an identifier such that the monitoring device may identify signals originating from that specific control unit. This may, for example, be effected by means of transmitting the signal from the control unit to the monitoring device at a unique frequency or by modulating the carrier signal with a unique signal that identifies the control unit. One monitoring device can thus advantageously be used to provide representations of measured physiological variables originating from a number of control units.

In an embodiment of the present invention, the guide wire is at a proximal portion arranged with a male connector. The control unit is connected to the guide wire by means of a female connector, which is interconnected with the male connector. This embodiment has the advantage that size requirements on the control unit becomes rather moderate.

In another embodiment of the present invention, the control unit is integrated with the guide wire at a proximal portion of the guide wire. In this particular embodiment, an interconnection of a male-female connector is avoided for connecting the control unit to the guide wire. When a physician places the guide wire into the appropriate location in the body, the male connector may be contaminated by, for example, dirt, fat, moist, etc., which is attached to the physician's fingers and deposited onto the male connector. Alternatively, body fluids such as blood may be deposited onto the connector when the guide wire is inserted in the body. In another scenario, to permit replacement or exchange of the catheter, the male connector is disconnected from the female connector and the catheter is removed over the guide wire. At that time, body fluids will be deposited directly onto the male connector and indirectly onto the female connector, via the male connector. Hence, the connectors may be contaminated by blood and other bodily fluids at the time the catheter is changed, and these body fluids will potentially alter the electrical properties of the connector. As a further consequence, the contaminations given above may deteriorate insulation between conductor members in the connectors, and give rise to leakage currents.

According to still another embodiment of the present invention, the control unit is arranged such that it may be powered via a power supply interface. Typically, a power source in the form of a DC battery is arranged at the control unit to provide the control unit with a sufficient supply voltage via the power supply interface. This has the advantage that the measurement system does not have to rely on the monitoring device for a supply voltage. In another embodiment, the control unit is provided with both the radio frequency interface and the power supply interface. Further, a switch is arranged to selectively provide the control unit with a supply voltage from the radio frequency interface or the power supply interface. The battery may thus be used as a back-up, or complement, to the power delivered by the monitoring device. Monitoring device power may also be employed to charge the battery.

According to a further embodiment of the invention, the radio frequency interface of the control unit is arranged such that communication of the control unit supply voltage is performed by means of inductive coupling between the control unit and the device with which it is communicating via the radio frequency interface. By employing an inductive coupling in the wireless interface, relatively low operating frequencies may be employed in the system, which has the advantage that the system becomes less sensitive to electromagnetic disturbances.

According to yet another embodiment, the radio frequency interface of the control unit is arranged such that communication of the measured physiological variables and the control data is performed by means of capacitive coupling between the control unit and the device with which it is communicating via the radio frequency interface. By employing a capacitive coupling in the wireless interface, small size components may be employed as compared to the case when inductors are employed.

In the light of the two preceding embodiments, it is clearly understood that the radio frequency interface may be either inductive, capacitive or a combination of both. Hence, some signals transferred across the wireless communication interface may be inductively transferred, while others may be capacitively transferred.

The present invention may advantageously be implemented in RFID (radio frequency identification) applications, in which applications the use of electromagnetic or electrostatic coupling is used to transfer energy between a tag/transponder (i.e. the control unit) and a reader/transceiver (i.e. the monitoring device). The transceiver sends RF energy that activates the transponder. When activated, the transponder typically transmits data back to the transceiver.

In further embodiments of the present invention, multiple access techniques are used to communicate the signal representing the measured physiological variable via the wireless interface to e.g. a monitoring device. When using a multiple access technique, multiple users may share the same frequency band. Three main methods are used when implementing multiple access: frequency division multiple access (FDMA), time division multiple access (TDMA) and code division multiple access (CDMA). Any one of these three technologies, or a combination thereof, may advantageously be employed in embodiments of the present invention.

Further features of, and advantages with, the present invention will become apparent when studying the appended claims and the following description. Those skilled in the art realize that different features of the present invention can be combined to create embodiments other than those described in the following.

BRIEF DESCRIPTION OF THE DRAWINGS

The preferred embodiments of the present invention will be described in more detail with reference made to the attached drawings, in which:

FIG. 12 shows an embodiment of the invention in which inductive coupling is employed; and FIG. 13 shows an embodiment of the invention in which a combination of inductive coupling and capacitive coupling is employed.

DETAILED DESCRIPTION OF THE PREFERRED EMBODIMENTS OF THE PRESENT INVENTION

In the prior art, it is known to mount a sensor on a guide wire and to position the sensor via the guide wire in a blood vessel in a living body to detect a physical parameter, such as pressure or temperature. The sensor includes elements that are directly or indirectly sensitive to the parameter. Numerous patents describing different types of sensors for measuring physiological parameters are owned by the applicant of the present patent application. For example, temperature could be measured by observing the resistance of a conductor having temperature sensitive resistance as described in U.S. Pat. No. 6,615,067. Another exemplifying sensor may be found in U.S. Pat. No. 6,167,763, in which blood flow exerts pressure on the sensor which delivers a signal representative of the exerted pressure. Both these U.S. patents are incorporated herein by reference.

In order to power the sensor and to communicate signals representing the measured physiological variable to a control unit disposed outside the body, one or more cables for transmitting the signals are connected to the sensor, and are routed along the guide wire to be passed out from the vessel to the external control unit via a connector assembly. In addition, the guide wire is typically provided with a central metal wire (core wire) serving as a support for the sensor.

Figure 1:
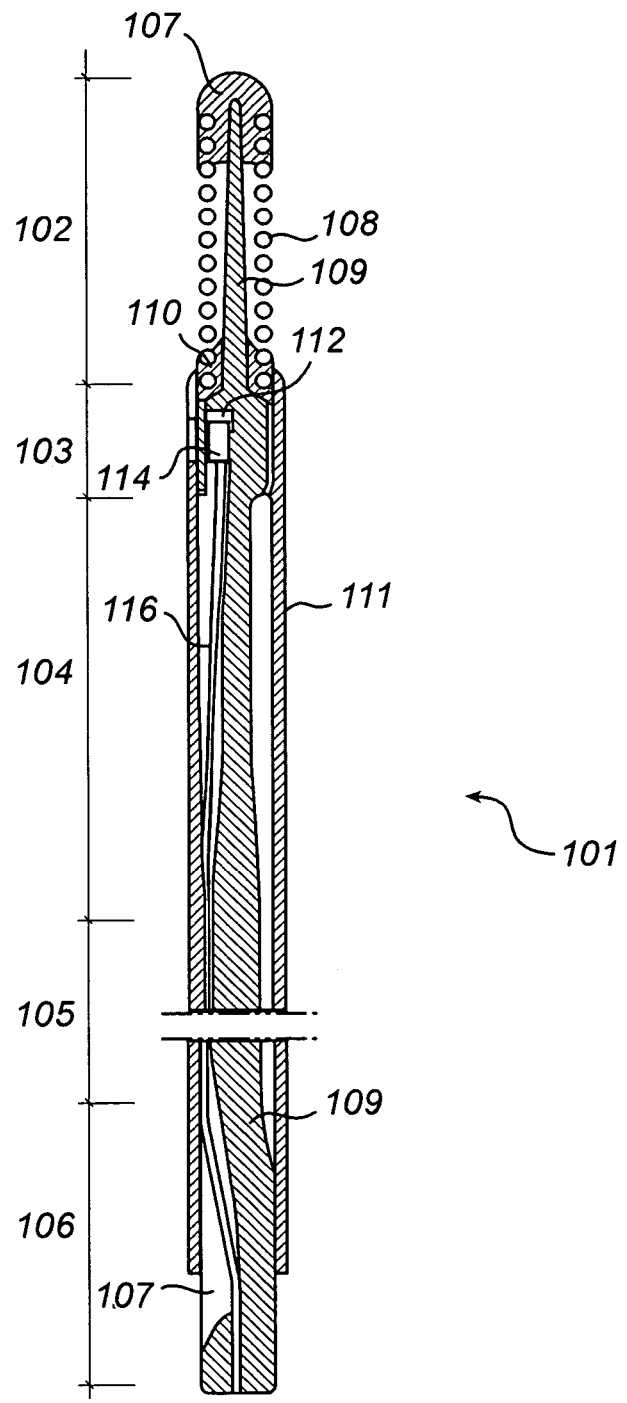
FIG. 1 shows a longitudinal section view of an exemplifying sensor guide construction that may be employed in the present invention.

FIG. 1 shows an exemplifying sensor mounted on a guide wire, i.e. a sensor guide construction 101. The sensor guide construction has, in the drawing, been divided into five sections, 102-106, for illustrative purposes. The section 102 is the most distal portion, i.e. that portion which is going to be inserted farthest into the vessel, and section 106 is the most proximal portion, i.e. that portion being situated closest to a not shown control unit. Section 102 comprises a radiopaque coil 108 made of e.g. platinum, provided with an arced tip 107. In the platinum coil and the tip, there is also attached a stainless, solid metal wire 109, which in section 102 is formed like a thin conical tip and functions as a security thread for the platinum coil 108. The successive tapering of the metal wire 109 in section 102 towards the arced tip 107 results in that the front portion of the sensor guide construction becomes successively softer.

At the transition between the sections 102 and 103, the lower end of the coil 108 is attached to the wire 109 with glue or alternatively, solder, thereby forming a joint 110. At the joint 110 a thin outer tube 111 commences which is made of a biocompatible material, e.g. polyimid, and extends downwards all the way to section 106. The tube 111 has been treated to give the sensor guide construction a smooth outer surface with low friction. The metal wire 109 is heavily expanded in section 103 and is in this expansion provided with a slot 112 in which a sensor element 114 is arranged, e.g. a pressure gauge. The sensor requires electric energy for its operation. The expansion of the metal wire 109 in which the sensor element 114 is attached decreases the stress exerted on the sensor element 114 in sharp vessel bends.

From the sensor element 114 there is arranged a signal transmitting cable 116, which typically comprises one or more electric cables. The signal transmitting cable 116 extends from the sensor element 114 to a (not shown) control unit being situated below the section 106 and outside the body. A supply voltage is fed to the sensor via the transmitting cable 116 (or cables). The signals representing the measured physiological variable is also transferred along the transmitting cable 116. The metal wire 109 is substantially thinner in the beginning of section 104 to obtain good flexibility of the front portion of the sensor guide construction. In the end of section 104 and in the whole of section 105, the metal wire 109 is thicker in order to make it easier to push the sensor guide construction 101 forward in the vessel. In section 106 the metal wire 109 is as coarse as possible to be easy to handle and is here provided with a slot 120 in which the cable 116 is attached with e.g. glue.

In a preferred embodiment of the present invention, the transmitting cable 116 is integrated with the core wire 119 of the guide wire. Using the core wire 119 as the transmitting cable reduces the number of components, since the separate transmitting cable shown in FIG. 1 thus may be omitted. However, it is clear that the method for communicating with the sensor described herein could be practiced with a separate transmitting cable, or a number of transmitting cables, running along the guide wire, or running along another path, as shown in FIG. 1. In case the core wire 119 is employed as the transmitting cable, the core wire 119 itself constitutes a first electric pole, and the thin outer tube 111 constitutes a second electric pole.

Figure 2:
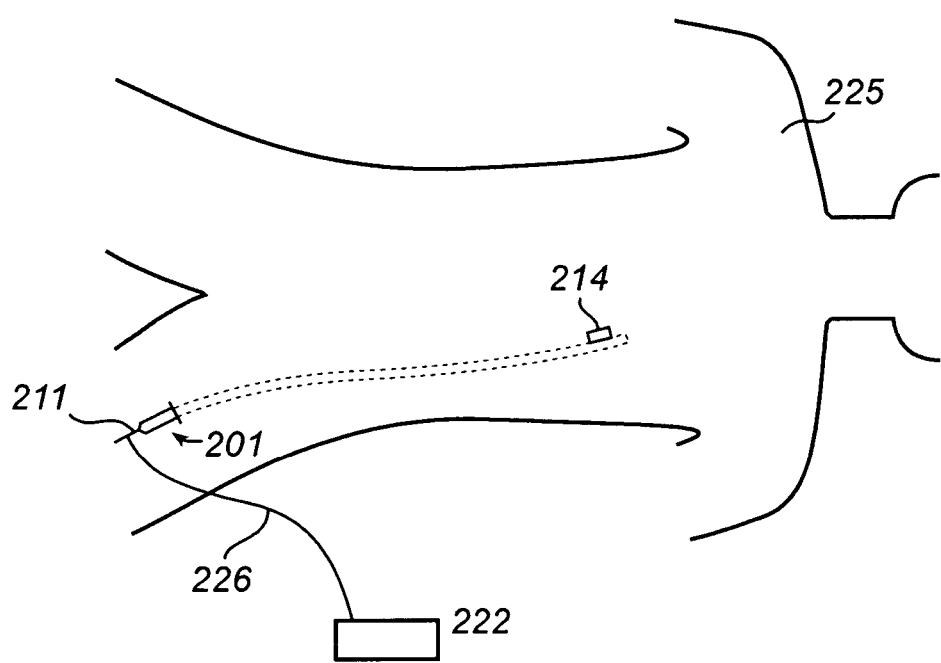
FIG. 2 shows a system for measuring a physiological variable in a body according to an embodiment of the present invention.

The use of a guide wire 201 according to the present invention, such as is illustrated in FIG. 1, is schematically shown in FIG. 2. Guide wire 201 is inserted into the femoral artery of a patient 225. The position of guide wire 201 and the sensor 214 inside the body is illustrated with dotted lines. Guide wire 201, and more specifically core wire 211 thereof, is also coupled to a control unit 222 via a wire 226 that is connected to core wire 211 using any suitable connector means (not shown), such as a crocodile clip-type connector or any other known connector. The wire 226 is preferably made as short as possible for easiness in handling the guide wire 201. Preferably, the wire 226 is omitted, such that the control unit 222 is directly attached to the core wire 211 via suitable connectors. The control unit 222 provides an electrical voltage to the circuit comprising wire 226, core wire 211 of the guide wire 201 and the sensor 214. Moreover, the signal representing the measured physiological variable is transferred from the sensor 214 via the core wire 211 to the control unit 222. The method to introduce the guide wire 201 is well known to those skilled in the art.

The voltage provided to the sensor by the control unit could be an AC or a DC voltage. Generally, in the case of applying an AC voltage, the sensor is typically connected to a circuit that includes a rectifier that transforms the AC voltage to a DC voltage for driving the sensor selected to be sensitive to the physical parameter to be investigated.

Figure 3:
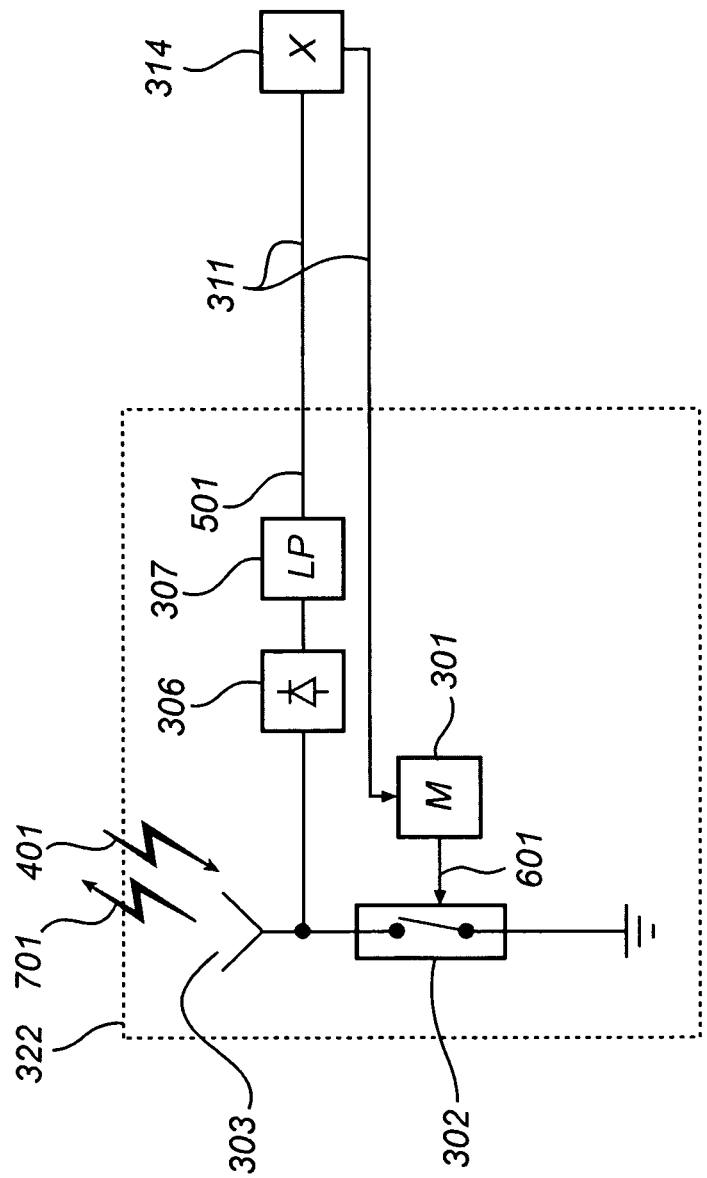
FIG. 3 shows a principal block scheme of a system for measuring a physiological variable in a body according to a preferred embodiment of the present invention.
Figure 4:
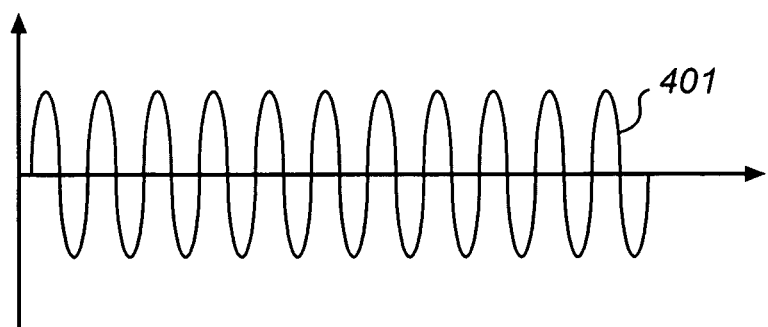
FIG. 4 shows a schematic diagram of an RF power signal employed to provide a sensor with a supply voltage.

FIG. 3 shows a principal block scheme of a system for measuring a physiological variable in a body according to a preferred embodiment of the present invention. The system comprises a control unit 322, a core wire 311 and a sensor 314. The control unit comprises a modulator 301, which typically consists of digital logic and sequential circuitry, preferably designed by CMOS (complementary metal oxide semiconductor) technology for the purpose of low power consumption. The control unit further comprises a switch 302, which may be a single transistor, either a bipolar or a field effect transistor, depending on the type of modulation, operating frequency etc. The function of the switch will be described in more detail hereinafter. The control unit also comprises an antenna 303 for receiving and transmitting RF signals. The RF operating frequency is typically about 125 kHz in case inductive coupling is employed, as will described in the following. The schematic diagram of FIG. 4 illustrates, in a non-scalar way, a received RF voltage 401 as a function of time.

Figure 5:
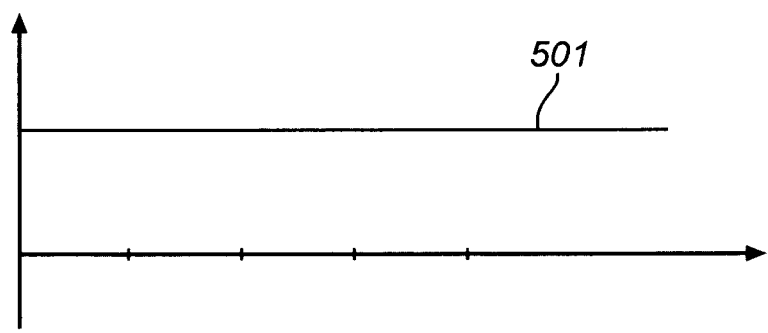
FIG. 5 shows a schematic diagram of a rectified voltage supplied to a sensor.

The control unit 322 of FIG. 3 further includes means for converting power received via the antenna 303 into a local voltage. The RF voltage of FIG. 4 is input to a rectifier 306, for example a Schottky diode in the case of a very high frequency or a pn-semiconductor in the case of a more moderate frequency. The rectified voltage passes through a low-pass filter 307 and then serves as a supply voltage for the micro-sensor 314. Note that, even though it is not shown in FIG. 3, the control unit 322 also extracts a supply voltage from the RF voltage 401 for feeding the control unit electronics. The signal 501 between the low-pass filter 307 and the micro-sensor 314 is schematically illustrated in the diagram of FIG. 5, showing the constant rectified voltage 501 as a function of time.

Figure 6:
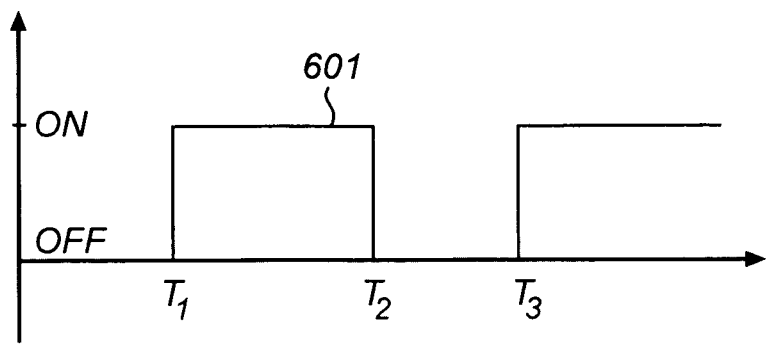
FIG. 6 shows a schematic diagram of an output signal from a modulator in a control unit in accordance with an embodiment of the present invention.

The micro-sensor 314 responds to the physiological variable, such as pressure, flow, temperature etc, that is to be measured and provides an output signal corresponding to the variable. It may operate on a resistive, capacitive, piezoelectric or optical principle of operation, according to well-established practice of sensor design. The modulator 301 converts the output signal of the micro-sensor 314 into a temporally coded signal, according to a specified scheme or algorithm, for example pulse-width modulation (PWM), frequency modulation (FM) etc. or some other well-established modulation scheme. The modulation is fed back to the antenna 303 via the guide wire 311 and the switch 302. The output signal 601 of the modulator 301 is schematically shown in FIG. 6. As is shown in FIG. 6, the output signal is OFF up to time T1. Between time T1 and T2, the output signal is ON, after which it again cut OFF. At time T3 it is again ON, and so on.

Figure 7:
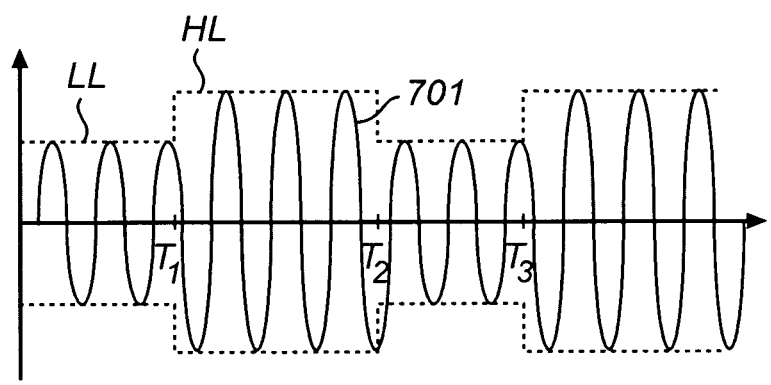
FIG. 7 shows a schematic diagram of a signal received by a demodulator in a receiver in accordance with an embodiment of the present invention.
Figure 8:
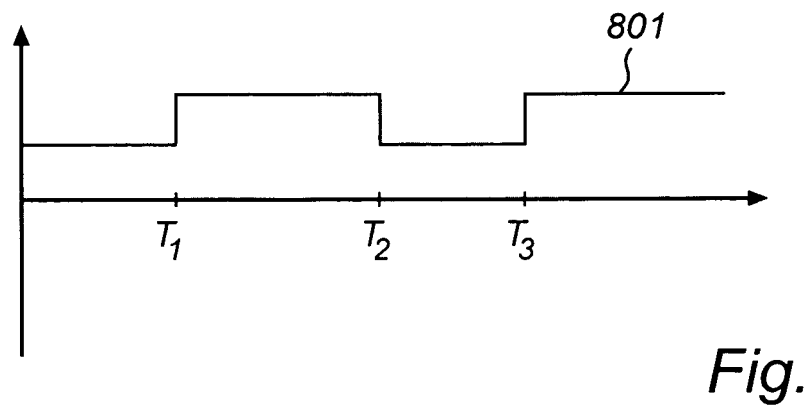
FIG. 8 shows a schematic diagram of a demodulated signal.

Thus, the power absorbed by the sensor 314 is influenced by the action of the switch 302, such that the absorption is different when the switch is in the ON state or the OFF state. The radio frequency voltage 701 detected by a receiver (not shown) will exhibit a higher level HL during the time interval between T1 and T2, and a lower level LL before time T1 and during the time interval between T2 and T3 etc., as is illustrated in FIG. 7. This enables information of the measured variable superimposed onto the transmitted electromagnetic field to be extracted by a demodulator (not shown) of the receiver of the signal 701, thereby producing a signal 801, as is seen in FIG. 8, having substantially the same temporal properties as the output signal 601 from the modulator 301, i.e. each change from a "high" to a "low" occurs at substantially the same point in time for the signal 601 from the modulator and the signal 801 from the demodulator. Thereby, the temporal information included in the signal can be extracted.

Any useful algorithm to transfer a measure of the physical variable to a characteristic value represented with one or several intervals of high or low absorption of the radio frequency voltage 401 could be selected. For example, the modulator 301 could be adapted to close the switch 302 for a time interval directly proportional to the measured variable. Of course the variable could be measured repeatedly at selected intervals, each of said measurements initiating the modulator to close the switch for an appropriate length of time. As an alternative, a measured value could be frequency coded in such a way that the modulator 301 closes the switch 302 a selected number of times for a given time interval, corresponding to a predetermined level of the measured variable.

Note that, as previously mentioned, the block scheme of FIG. 3 is illustrative to provide a description of an exemplifying embodiment of the present invention. In practice, it is envisaged that standard circuits are used. For example, as a control unit 322, a U3280M transponder interface for a microcontroller from Atmel may be employed. If that type of standard circuitry is employed, a microcontroller is also typically used for handling communication to/from and control of the U3280M circuit. This generally also requires A/D converters, memories and other peripheral electronics, as realized by the skilled person.

Figure 9:
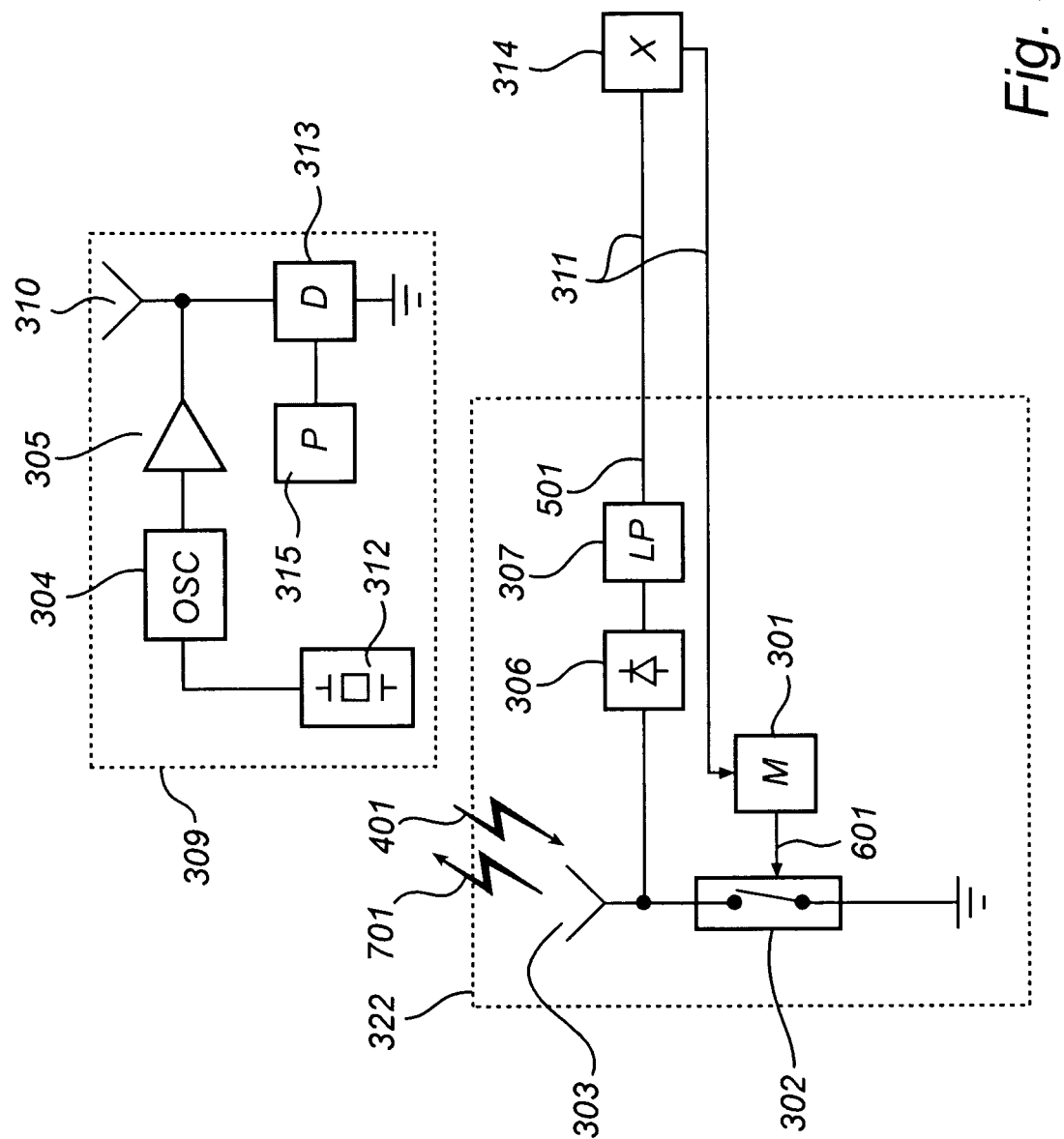
FIG. 9 shows a principal block scheme of a system for measuring a physiological variable in a body according to an embodiment of the present invention, which system includes a monitoring device for providing a representation of the measure variable.

In FIG. 9, another embodiment of the present invention is shown, in which the system for measuring a physiological variable in a body further comprises a monitoring device 309 arranged to demodulate the modulated signal 701, which modulated signal is received via an RF interface, and hence provide a representation of the measured physiological variable. The monitoring device may further be arranged to supply the control unit with the supply voltage 401 and control data via the RF interface. When performing this type of physiological measurement, there is generally a need for a monitoring device, such as a computer and an associated computer screen, for monitoring the signals the represent the measured variables after demodulation. The monitoring device is typically connected to the mains supply, from which a 230V AC voltage may be provided. Since the parts of the system of the present invention that are located in vicinity of the object on which measurements are performed, i.e. the control unit, the sensor and related circuitry, preferably should be as small as possible in order to simplify management of the measurement system during operation, it is advantageous if the monitoring device can provide the system with a sufficient supply voltage, since any power source arranged at the control unit thus may be eliminated. Control data transmitted from the monitoring device 309 to the control unit 322 are typically processed at the control unit by a microcontroller (not shown).

The monitoring device 309 includes a transmitting path and a receiving path for wireless transmission and reception of modulated/demodulated signals over a communication interface. The transmitting path of the monitoring device 309 includes a narrow-band oscillator 304, an amplifier 305 and an antenna 310. RF waves 401 of substantially constant amplitude and frequency are emitted by the antenna 310 at the operating frequency of the oscillator 304. In order to control and maintain the oscillating frequency at a constant or controllable frequency, adequate signal generating means such as a quartz crystal 312 is included. With a quartz crystal, it is possible to ensure a frequency stability of $10^{-6}$ or better. This is of importance both for the immunity against electromagnetic interference of the system, and to avoid undesired induced interference from the system to other electronic equipment. The schematic diagram of FIG. 4 illustrates, in a non-scalar way, the transmitted RF voltage 401 as a function of time.

The monitoring device 309 further includes a demodulator 313. The demodulator 313 converts the time or frequency coded signal 701 back to a sensor signal, according to an inverse algorithm as that of the modulator 301. The monitoring device 309 also includes means for signal processing and presentation 315. The amplifier 305 is preferably of the type known in the literature as phase-sensitive, phase-tracking, or synchronous. The bandwidth of such an amplifier can be extremely small. The system according to the invention is preferably operating at an extremely small bandwidth in order to minimize the influence of electromagnetic disturbances.

Figure 10:
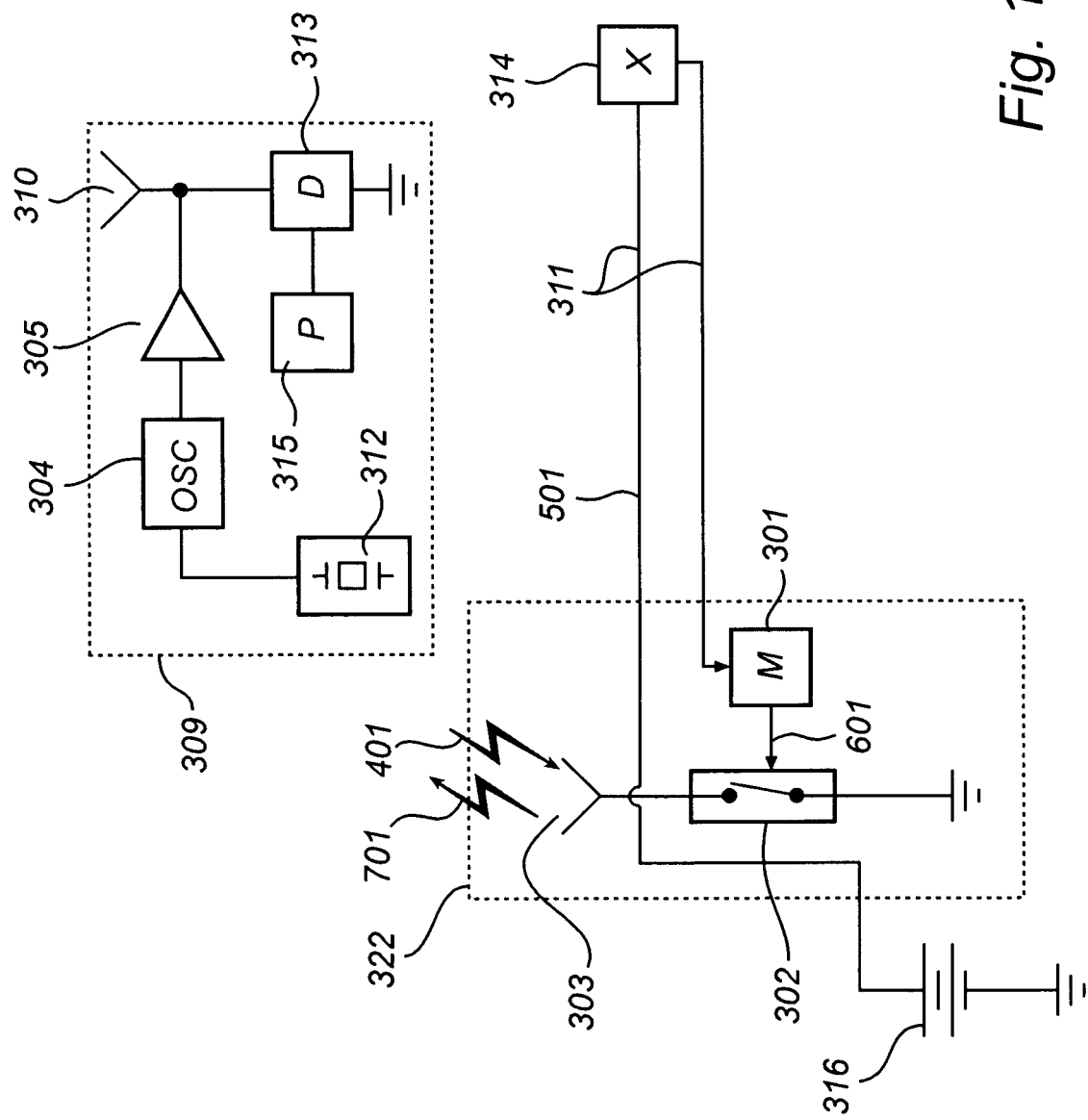
FIG. 10 shows a principal block scheme of a system for measuring a physiological variable in a body according to an embodiment of the present invention, which system includes a power source for supply voltage provision via a power supply interface.

FIG. 10 shows another embodiment of the invention, in which the control unit 322, and hence the sensor 314, is powered by a power source in the form of a battery 316 via a power supply interface. In this case, the supply voltage provided to the sensor 314 via the guide wire 311 is a DC voltage. There is thus no need for a rectifier and an LP filter arranged at the control unit 322. The control unit electronics are also powered by the battery 316. It is clearly understood that the power source not necessarily comprises a battery, but may also comprise, for example, a capacitor that may be charged and discharged.

Figure 11:
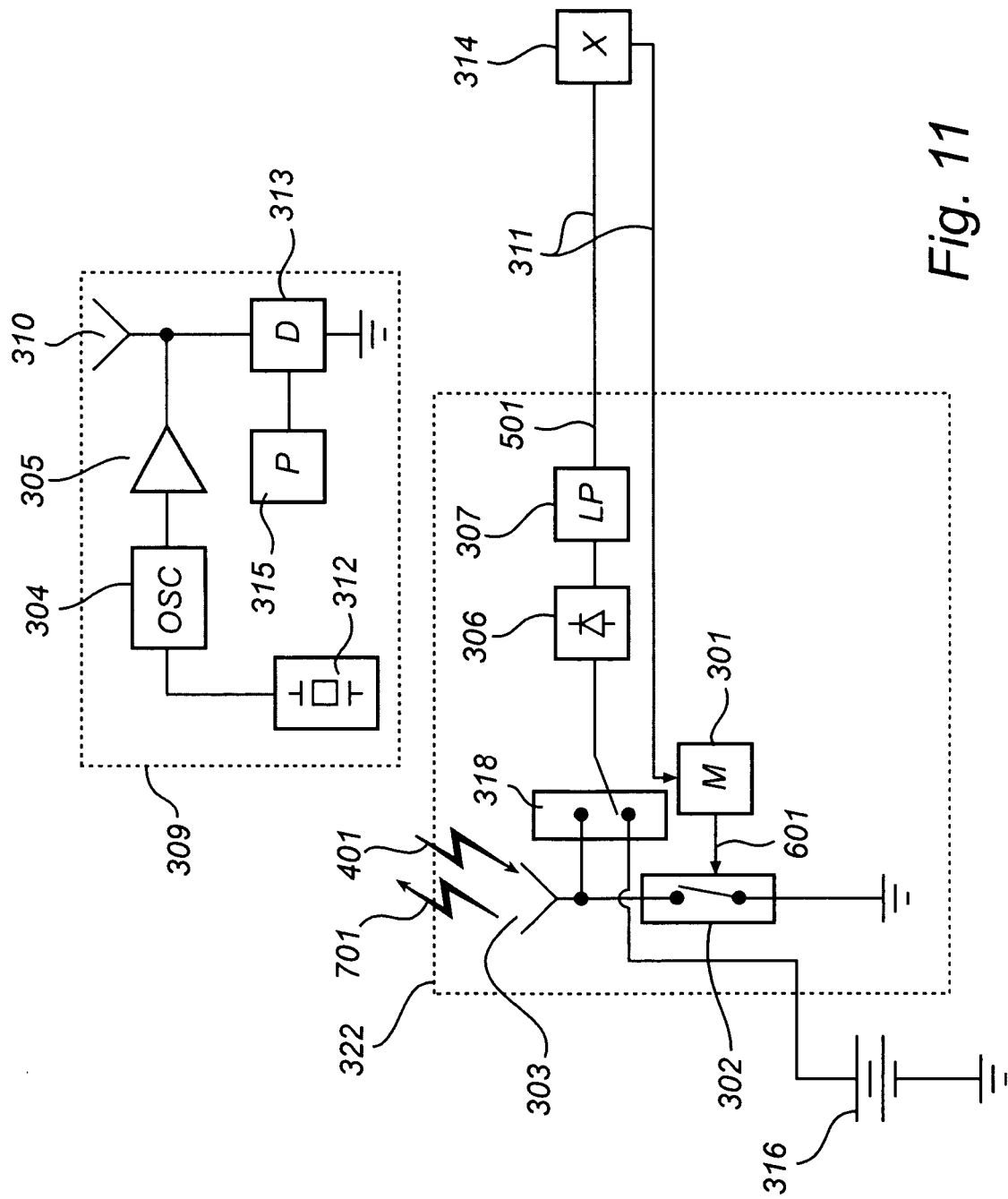
FIG. 11 shows a principal block scheme of a system for measuring a physiological variable in a body according to an embodiment of the present invention, which system comprises a switch arranged to selectively provide the control unit with a supply voltage from the RF interface or the power supply interface.

In FIG. 11, a switch 318 is provided such that the control unit 322 selectively can chose to supply the sensor 314 from the battery 316 or by means of the RF signal 401. Advantageously, the U3280M transponder interface from Atmel has this feature implemented. The battery 316 is in that case not necessarily used as a primary source of power for the control unit 322 and the sensor 314, but can be considered to be a back-up, or a complement, to the RF signal 401. It is also possible that the battery 316 may be charged by the RF signal 401.

FIG. 12 shows an embodiment of the present invention, in which the RF interface of the control unit 322 is arranged such that communication of the control unit supply voltage 330 and control data and signals 340 representing measured variables is performed by means of inductive coupling between the control unit and the device with which it is communicating via the RF interface, for example the monitoring device 309. By employing an inductive coupling in the wireless interface, relatively low operating frequencies may be employed in the system, which has the advantage that the system becomes less sensitive to electromagnetic disturbances. Moreover, inductive coupling enables transmission over greater distances.

FIG. 13 shows an embodiment of the present invention, in which the RF interface of the control unit 322 is arranged such that communication of the control unit supply voltage 330 is performed by inductive coupling and control data and signals 340 representing measured variables is performed by means of capacitive coupling between the control unit and the device with which it is communicating via the RF interface, for example the monitoring device 309. By employing a capacitive coupling in the wireless interface, small size components may be employed as compared to the case when inductors are employed.

In the light of the two preceding embodiments, it is clearly understood that the radio frequency interface may be either inductive, capacitive or a combination of both. Hence, some signals transferred across the wireless communication interface may be inductively transferred, while others may be capacitively transferred.

In embodiments of the present invention, communication via the wireless communication interface are undertaken by means of using spread spectrum techniques.

If direct sequence spread spectrum (DSSS) is employed, the signal representing the measured physiological variable, i.e. the baseband signal, is multiplied by a high-frequency PN-sequence to spread the baseband signal over a wider bandwidth. At the monitoring device, the spread signal is multiplied with an exact replica of the PN-sequence to recover the original baseband signal. Binary phase shift keying (BPSK) may be employed to modulate the carrier signal with the signal representing the physiological variable in DSSS.

When employing frequency hopping spread spectrum (FHSS), the frequency of the carrier signal (on which the signal representing the measured physiological variable is modulated) is "hopped" according to a code similar to the PN-sequence used in DSSS. At the monitoring device, a receiver performs similar frequency hopping to stay in tune with the frequency hopping performed at the control unit. Note that FHSS is divided into fast and slow hopping; fast FHSS performs more than one hop for each transmitted symbol whereas slow FHSS transmits multiple symbols before hopping to the next frequency. Gaussian minimum shift keying (GMSK) may be used for modulation in FHSS, which makes for a fair tradeoff between power and spectral efficiency.

It should be noted that hybrid spread spectrum techniques may be used, such as e.g. a combination of DSSS and FHSS.

Further, multiple access techniques such as FDMA, TDMA and CDMA may be employed for communicating the signal representing the measured physiological variable via the wireless communication interface.

In FDMA, each user is allocated a unique carrier frequency, and no other user is allowed to use the channel that corresponds to that carrier. FDMA has a hard limit on the maximum number of simultaneous users, since there is no room for an additional user once all channels are occupied.

In TDMA, each user is allocated unique time slots within each channel. In a channel, a user will only transmit or receive during a portion of the total channel time. Hence, the users must be synchronized. As in FDMA, there is a hard limit on the maximum number of users allowed.

In CDMA, a spread spectrum technique such as DSSS or FHSS is used, where different users are allocated different PN-sequences. Each user is discriminated by her orthogonal PN-sequence. In CDMA, there is a soft limit on the maximum number of users. Increasing the number of users linearly raises the noise floor, which gradually deteriorates the channel.

A combination of the above mentioned different multiple access techniques is possible. For instance, in GSM, TDMA is used in conjunction with FDMA. In third generation cellular phones (WCDMA/3GPP and IS-95), CDMA is used in combination with FDMA.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

The invention claimed is:

1. A system for measuring a physiological variable in a body, which system comprises:
   a sensor arranged to be disposed in the body, the sensor being configured to measure the physiological variable and to provide a signal representing the measured physiological variable;
   a battery;
   a control unit configured to be disposed outside the body; and
   a wired connection between the sensor and the control unit to provide a supply voltage from the control unit to the sensor, and to communicate said signal from the sensor to the control unit,
   wherein the control unit comprises:
      a modulator configured to modulate a carrier signal with the signal representing the measured physiological variable, which is received by the control unit, to provide a modulated signal, and
      a communication interface configured to communicate the modulated signal by wireless spread spectrum communication,
   wherein the wired connection comprises a guide wire configured to position the sensor within the body,
   wherein the control unit is configured such that a path between the communication interface and a device receiving the wireless spread spectrum communication does not pass through tissue,
   wherein the battery provides power to the control unit and to the sensor.

2. The system according to claim 1, further comprising:
   the device configured to communicate via the communication interface, to demodulate the modulated signal which is wirelessly received via the communication interface, and to provide a representation of the measured physiological variable.

3. The system according to claim 2, wherein the monitoring device is configured to communicate via the communication interface, to demodulate a number of modulated signals wirelessly received via the communication interface from a number of control units, and to provide a representation of measured physiological variables that correspond to the received modulated signals.

4. The system according to claim 3, wherein each modulated signal wirelessly received via the communication interface from a number of control units is provided with an identifier such that each control unit may be identified by the modulated signal for each control unit.

5. The system according to claim 1, wherein the signal representing the measured physiological variable is communicated via the communication interface using direct sequence spread spectrum.

6. The system according to claim 1, wherein the signal representing the measured physiological variable is communicated via the communication interface using frequency hopping spread spectrum.

7. The system according to claim 2, wherein the monitoring device is further arranged to supply the control unit with a supply voltage and control data via the communication interface.

8. The system according to claim 7, further comprising: a switch configured to selectively provide the control unit with a supply voltage from the communication interface or a power supply interface.

9. The system according to claim 1, wherein the control unit is configured such that the control unit may be powered via a power supply interface.

10. The system according to claim 9, wherein the control unit further comprises a power source configured to provide the control unit with a supply voltage via the power supply interface.

11. The system according to claim 1, wherein the communication interface of the control unit is configured such that communication is performed by inductive coupling between the control unit and the device with which the control unit is communicating via the communication interface.

12. The system according to claim 11, wherein the communication interface of the control unit is arranged such that communication of a control unit supply voltage is performed by inductive coupling between the control unit and the device with which the control unit is communicating via the communication interface.

13. The system according to claim 11, wherein the communication interface of the control unit is configured such that communication of the measured physiological variable and control data is performed by capacitive coupling between the control unit and the device with which the control unit is communicating via the communication interface.

14. The system according to claim 1, wherein the communication interface of the control unit is configured such that communication is performed by capacitive coupling between the control unit and the device with which the control unit is communicating via the communication interface.

15. The system according to claim 1, wherein a core wire of the guide wire constitutes a first electric pole, and an outer tube of the guide wire constitutes a second electric pole.

16. The system according to claim 1, wherein the wired connection includes a male connector at a proximal portion, and the control unit is configured to be connected to the wired connection via a female connector to be interconnected with said male connector.

17. The system according to claim 1, wherein the control unit is integrated with the wired connection at a proximal portion of said connection.

18. The system according to claim 1, wherein the system is configured to employ a multiple access technique to communicate the signal representing the measured physiological variable via the communication.

19. The system according to claim 18, wherein the multiple access technique comprises frequency division multiple access (FDMA).

20. The system according to claim 18, wherein the multiple access technique comprises time division multiple access (TDMA).

21. The system according to claim 18, wherein the multiple access technique comprises code division multiple access (CDMA).

22. The system according to claim 1, wherein the control unit is configured to also receive power via a wireless transmission.

23. The system according to claim 22, wherein the control unit can choose to supply the sensor with power from either the battery or from the wireless transmission.

24. The system according to claim 1, wherein the battery can be charged by the wireless transmission.

25. A method of measuring a physiological variable in a body, which method comprises the steps of:
   measuring the physiological variable with a sensor disposed in the body;
   communicating, via a wired connection, a signal representing the measured physiological variable from the sensor to a position outside the body;
   supplying, via the wired connection, the sensor with a supply voltage;
   modulating, at the position outside the body, a carrier signal with the signal that represents the measured physiological variable to provide a modulated signal; and
   communicating the modulated signal wirelessly using spread spectrum communication to a remote position,
   wherein the wired connection comprises a guide wire configured to position the sensor within the body,
   wherein the step of communicating the modulated signal wirelessly comprises sending the modulated signal along a path to the remote position that does not pass through tissue,
   wherein said position outside the body comprises a control unit with a wireless interface,
   wherein a battery at said position outside the body provides power to the control unit and to the sensor.

26. The method according to claim 25, further comprising the steps of:
   receiving the modulated signal at the remote position;
   demodulating the received modulated signal; and
   providing a representation of the measured physiological variable for further use.

27. The method according to claim 25, further comprising the step of:
   wirelessly supplying, from the remote position, the control unit with the supply voltage and control data.

28. The method according to claim 25, further comprising the step of:
   supplying, via a power supply interface, the control unit with the supply voltage.

29. The method according to claim 27, further comprising the step of:
   selectively supplying, via a switch , the control unit with the supply voltage from a communication interface or a power supply interface.

30. The method according to claim 25, wherein the signal representing the measured physiological variable is communicated to a remote position by direct sequence spread spectrum.

31. The method according to claim 25, wherein the signal representing the measured physiological variable is communicated to a remote position by frequency hopping spread spectrum.

32. The method according to claim 25, wherein the signal representing the measured physiological variable is communicated via a communication wireless interface by a multiple access technique.

33. The method according to claim 32, wherein the multiple access technique comprises frequency division multiple access (FDMA).

34. The method according to claim 32, wherein the multiple access technique comprises time division multiple access (TDMA).

35. The method according to claim 32, wherein the multiple access technique comprises code division multiple access (CDMA).

36. The method according to claim 25, wherein the control unit is configured to also receive power via a wireless transmission.

37. The method according to claim 36, wherein the control unit can choose to supply the sensor with power from either the battery or from the wireless transmission.

38. The method according to claim 36, wherein the battery can be charged by the wireless transmission.

* * * * *